United States Patent [19]

Thompson

[11] Patent Number: 5,308,611
[45] Date of Patent: May 3, 1994

[54] ANTISEPTIC COMPOSITION

[75] Inventor: Cedric B. H. Thompson, Surrey, Canada

[73] Assignee: Stanley Pharmaceuticals Ltd., North Vancouver

[21] Appl. No.: 864,124

[22] Filed: Apr. 6, 1992

Related U.S. Application Data

[63] Continuation of Ser. No. 493,191, Mar. 14, 1990, abandoned.

[51] Int. Cl.$^5$ .............................................. A61K 31/00
[52] U.S. Cl. .............................. 424/78.07; 424/78.08; 424/78.37
[58] Field of Search .............. 424/78, DIG. 14, 78.08, 424/78.07, 78.37; 514/482, 483

[56] References Cited

U.S. PATENT DOCUMENTS

| T943,010 | 2/1976 | Pettoruto | 514/555 |
| 4,199,567 | 4/1980 | Rankin | 424/173 |
| 4,466,975 | 8/1984 | Magani et al. | 514/373 |

OTHER PUBLICATIONS

Lilly et al Brit. Med. Journal pp. 510–515 1973(1).

*Primary Examiner*—Thurman K. Page
*Assistant Examiner*—Peter F. Kulkosky
*Attorney, Agent, or Firm*—Christensen, O'Connor, Johnson & Kindness

[57] ABSTRACT

An antiseptic composition comprises a cidal agent and at least one nonionic surfactant selected from the group comprising alkyl phenyl macrogol ethers.

20 Claims, No Drawings

ANTISEPTIC COMPOSITION

This application is a continuation application based on prior copending application Ser. No. 07/493,191, filed on Mar. 14, 1990, abandoned.

FIELD OF THE INVENTION

This invention relates to antiseptic compositions, processes for making said compositions, and methods of employing said compositions. In particular, this invention relates to chlorhexidine-containing antiseptic compositions.

BACKGROUND OF THE INVENTION

Chlorhexidine, [1,6-di (4-chloro-phenyl-diguanido) hexane], is a widely used antiseptic or anti-infective in human medical and veterinary practice. Typically, it is used as a topical skin cleansing agent or antiseptic in cosmetic preparations, pharmaceutical and surgical scrubbing and shaving compositions and deodorants.

Currently on the market is a chlorhexidine digluconate-containing surgical scrub (Hibitane) which comprises a detergent base of polyoxyethylene-polyoxyproplyene block polymer (a nonionic surfactant) and dimethyllauryl amine oxide, an amphoteric surfactant. Although this preparation has generally been considered acceptable, an allergic reaction to the formulation has been found in some users.

U.S. Defensive Publication T943,010, which was published on Feb. 3, 1976 describes an aqueous foamable system comprising chlorhexidine and a nonionic surfactant. The surfactants disclosed are selected from combinations of polyoxyethylene ethers or partial hexitan esters of fatty acids having 12-24 carbon atoms, fatty alcohols, and polyoxyethylene derivatives of fatty alcohols having 10-18 carbon atoms, polyhydric materials such as sorbitol and carboxy-vinyl polymers. This publication is intended to provide a highly foamable chlorhexidine solution and accordingly, the surfactant is selected to provide this desired characteristic.

U.S. Pat. No. 4,199,567 to Burton Parsons & Company describes a method of rendering freeze-stable chlorhexidine-containing mediciments, in particular, ophthalmic solutions, by adding thereto a surfactant selected from polyoxyethylene derivatives of long chain fatty acid partial esters of hexitol anhydride.

U.S. Pat. No. 3,574,821 to Mediline A. G. describes an aerosol spray deodorant for use in feminine hygiene comprising an aerosol propellant, a bactericide such as chlorhexidine, a surfactant and an emollient. This patent is concerned only with an aerosol formulation suitable for use as a deodorant spray and the unique selection of ingredients and amounts are adapted therefor.

SUMMARY OF THE INVENTION

The present invention provides an antiseptic composition comprising a cidal agent and one or more nonionic surfactants selected from the group comprising alkyl phenyl macrogol ethers. Preferably, the cidal agent is chlorhexidine.

This composition may be used alone or in conjunction with other components to form a superior antiseptic treatment.

It has been found that this composition beneficially reduces the number of microrganisms at the application site as measured by Minimum Lethal Concentration (MLC studies.

This composition is particularly effective against many aerobic and anaerobic gram positive and gram negative bacteria including but not limited to those of the genera Corynebacterium, Enterococcus, Staphloycoccus, Streptococcus, Escherichia, and Klebsiella and fungi including but not limited to those of the genus Candida.

Also defined within the scope of the present invention are methods of employing the the novel compositions described herein to reduce the number of microrganisms at a given application site.

PREFERRED EMBODIMENTS

By way of definition, it is to be understood that "cidal" refers to the capability to kill microorganisms including bacteria and fungi.

In a preferred aspect, the cidal agent is chlorhexidine, and is provided in the composition as a water-soluble gluconate, acetate or hydrochloride. It is not intended, however, that this invention should be limited to these forms of chlorhexidine. Other satisfactory salts include chlorhexidine di-1-glutamate, chlorhexidine di-succinate, chlorhexidine di-iminodiacetate and chlorhexidine di-6-acetamidohexanoate. Of all of these salts, chlorhexidine gluconate, chlorhexidine acetate and chlorhexidine hydrochloride are preferred.

Alkyl phenyl macrogol ethers are condensation products prepared by the reaction between fatty alkyl phenols and ethylene oxide optionally with formaldehyde. The ether linkage in the substances confers good stability to acids and alkalis. Alkyl phenyl macrogol ethers are hydrophilic and water-soluble.

Preferably, the nonionic surfactant, which comprises one or more of the alkyl phenyl macrogol ethers, is selected from nonoxinols (macrogol nonyl-phenyl ethers), octoxinols (macrogol tetramethylbutylphenyl ethers), and tyloxapols (polymers of 4(1,1,3,3-tetramethyl butyl) phenol with ethylene oxide and formaldehyde).

More specifically, the alkyl phenyl macrogol ether may be selected from the group comprising nonoxinol 4, nonoxinol 9, nonoxinol 10, nonoxinol 15, nonoxinol 30 and octoxinol 9.

Most preferably, the nonionic surfactant is a nonoxinol, also known as alpha-(4-nonylphenyl)-w-hydroxypoly(oxyethylene). The nonoxinols are characterized by a series of nonylphenyl ethers of macrogols of differing chain lengths, represented by the formula:

$$C_{15}H_{23}[OCH_2CH_2]_nOH$$

Nonoxinol-4, nonoxinol-9, nonoxinol-10, nonoxinol-15 and nonoxinol-30 are illustrative of this group of alkyl phenyl macrogol ethers.

The most basic form of the antiseptic composition of the present invention comprises chlorhexidine and one or more nonionic surfactants as described herein.

The preferred form of the antiseptic composition is a liquid, although this is by no means the only form in which it may be provided. Other forms include but are not limited to pastes, jells, creams or aerosols.

Preferably, the composition comprises 0.05%-25% by weight chlorhexidine salt depending on the form in which the chlorhexidine is provided more preferably, 0.5%-10% by weight chlorhexidine salt, and 5%-30% by weight of the alkyl phenyl macrogol ether(s) depending on the nature of the chosen surfactant(s). It has been established that a more preferred composition comprises from 2-4% by weight chlorhexidine and from 5-20% by weight alkyl phenyl macrogol ether(s). Most preferably, however, the composition comprises 2% chlorhexidine and 7.5% alkyl phenyl macrogol ether or 4% chlorhexidine and 15% alkyl phenyl macrogol ether.

Optionally, one or more emollients may be added to the antiseptic composition. The choice of the emollient will depend on the softness desired in the end product. Preferred emollients include glycerin and polyhydric compounds selected from the group comprising sorbitol, mannitol and carboxy vinyl polymers. It is preferred that the emollient(s) comprises 1-10% of the antiseptic composition.

Optionally, one or more thickeners or stabilizers may be added to the antiseptic composition to obtain the desired consistency. It is well within the purview of a skilled artisan to select an appropriate thickener, however, the preferred thickeners for use in the present composition include, but are not limited to fatty acid alkyloamides selected from the group comprising coconut oil mono- or di- ethanolamide, coconut oil mono- or di- isopropanolamide, coconut oil diglycolamide, oleic diethanolamide and lauric diethanolamide an fatty amine oxides selected from the group comprising di-methyl cocamide oxide, dimethyl lauryl amine oxide, and dimethyl oleyl amine oxide. This latter group of compounds, the fatty amine oxides, may also increase the foaming capacity of the antiseptic composition. The polyhydric compounds, discussed hereinabove, may also serve as thickeners. Preferably, the thickener(s) is present in an amount from 1-10% of the composition.

Optionally, a moisture-retaining agent may be added to the antiseptic composition. These agents include, but are not limited to fatty alcohols such as cetyl and stearyl alcohol.

In a preferred form of the composition, colourings such as amaranth and sunset yellow may be added. The amount of the colourings will depend on the intensity of colour desired in the end product. The exact amount to be added is well within the skill of a technician.

If desired, other cationic and/or anionic cidal agents may be added to the antiseptic composition. Examples of these "secondary" cidal agents include the quarternary ammonium compounds. Similarly, along with the alkyl phenyl macrogol ether(s), other cationic and/or anionic surfactants may be included in the antiseptic composition.

It is recommended that the pH of the composition be maintained between 5 and 7.5. Most preferably, the pH of the composition should be about 6. The adjustment in pH may be achieved by many methods including the addition of one or more buffering agents such as acidifiers (e.g. citric acid, sodium citrate) to the composition during its formulation.

A most preferred composition comprises chlorhexidine gluconate, nonoxinol, glycerin, coconut oil diethanolamide, amaranth, sunset yellow, sodium citrate and citric acid.

The process for making the antiseptic composition of the present invention is as follows. The surfactant(s) is dissolved in an appropriate amount of water, preferably purified water. Chlorhexidine is then added to and dissolved in the surfactant-containing solution. After thorough mixing, the composition is ready to use in any number of applications as described herein.

It is suggested that the water used in the process in composition of the present invention be of superior grade and in a purified form. Preferred water quality standards are set out in the British Pharmacoepia (BP) and the U.S. Pharmacoepia (USP). Generally, the water should be low in salt and iron content. However, even water with a high iron concentration may be used if the water is appropriately pre-treated by the addition of a chelating agent such as EDTA and/or a softening agent.

In a *preferred* process of the present invention, the surfactant(s) is mixed and dissolved in purified water. While stirring the mixture, the chlorhexidine and optionally the emollient(s) and thickener(s) are added. The resultant mixture is subsequently cooled to room temperature, neutralized with an appropriate buffering agent and the colourings are added and dissolved. After mixing, the final composition may be filtered prior to storage.

It is recommended that all containers used in the process of the present invention are maintained relatively sterile and covered during the manufacturing steps to minimize contamination. It is also important to note that the composition should not be mixed too vigorously to prevent excessive sudsing.

It is preferred that the steps of the process, unless otherwise indicated, occur at room temperature.

The antiseptic composition as described herein has a superior ability to eliminate the number of microorganisms at the application site. This activity has been assessed using minimum lethal concentration (MLC) studies which are provided in the appended examples.

The antiseptic composition of the present invention is a successful and effective hand cleaner or scrub. It is particularly suited for use in hospitals, clinics and laboratories where the maximum elimination of microorganisms from the application site is demanded. The reduced foaming capacity of the composition reduces the amount of composition wasted at each wash and also reduces the rinsing time necessary to eliminate the residue of the composition from the application site.

In some instances, it may be desirable to add perfume or fragrance oils to the antiseptic composition, particularly when the cleanser is to be used by the general public.

Although particularly suitable as a hand cleaner, this is by no means the only use of the present composition. For example, the composition may be used as a full body cleanser or as a portion of a shaving or shampooing formulation.

It is understood that changes and variations may be made to the present invention by one skilled in the art without deviating from the spirit and scope thereof as defined in the specification and claims.

The following examples are offered by way of illustration and not by way of limitation.

EXAMPLE I

Preparation of a 2% Chlorhexidine Gluconate Antiseptic Composition

Water (Ex Aqua) (6000 L) was filtered through a micropore filter and transferred to an 8500 L tank. Seven percent w/v (637.5 L) nonoxinol 9 or nonyl phenol polyglycol ether condensate (Sterling NPX TM) was dissolved by mixing with the filtered water. The line was then flushed with more filtered water.

To the resultant solution was then added 10% w/v chlorhexidine gluconate (20% solution B.P.C.) or 850 L, 2.5 w/v glycerin U.S.P. or 212.5 kg, and 2.5% w/v coconut oil diethanolamide (Comperlan KD) or 212.5 kg. These additions were stirred and thoroughly dissolved in the surfactant-containing solution, and the solution was subsequently allowed to cool at room temperature.

After cooling, 0.006% w/v amaranth (FD and C red No. 2), or 0.510 kg and 0.005% w/v sunset yellow or 0.510 kg in 10 L of micropore filtered water was added to the cooled solution.

Citric acid hydrous 0.11% w/v or 9.35 kg and sodium citrate hydrous 0.025% w/v or 2.125 kg were dissolved in the cooled solution. Filtered water (about 500 L) was then added to the resultant solution to make a total volume of 8,500 L and an approximate pH of 6.0.

The resultant solution was then mixed for 1 hour and passed through a micropore filter.

EXAMPLE II

Preparation of a 4% Chlorhexidine Gluconate Antiseptic Composition

Following the steps outlined in Example I above, an antiseptic composition with the following formulation was prepared:

chlorhexidine gluconate 4% w/v
nonoxinol 9 15% w/v
glycerol 5% w/v
coconut oil diethonolamide 5.0% w/v
amaranth (FD+C Red #2) 0.0008% w/v
sunset yellow (FD+C Yellow #6) 0.001% w/v
citric acid 0.22% w/v
sodium citrate 0.09% w/v
water made up to 100% (using approx. 57% w/v)

EXAMPLE III

Analysis of Cidal Activity of Antiseptic Composition

The efficacy of an antiseptic composition is assessed most thoroughly by using the Time Kill Analysis Methodology. The principle behind this methodology is to express the disinfectant power of the composition in terms of its "Minimum Lethal Concentration" (MLC) which is the least concentration of the composition in ug/ml of active ingredient that results in a 99.99% decrease in viable count of the test micro-organism from zero time (To) exposure to the antiseptic composition under a set of specific test conditions.

In this Example, a comparison of the efficacies of a preferred composition of the present invention (4% chlorhexidine gluconate composition as described in Example II) and a commercially available hand cleansing product (4% Hibitane [Ayerst]) was made.

The Test Conditions were as follows:

| Exposure | |
|---|---|
| Time Intervals | 1, 2, 5 minutes |
| Temperature/ | 22 ± 1° C. |
| Final inoculum | 1 × 10$^8$ to 1 × 10$^9$ CFU/ml |
| End point | ≧99.99% decrease in the viable count from time 0 (T$_0$) |
| Strains | #1 to #70 (70 varieties of aerobic hospital isolates & QC strains tested) |
| Dilution range | The active ingredient chlorhexidine gluconate was diluted to: 1, 10, 50, 100, 200, 500, 1000, 2000 ug/ml (.0001, .001, .005, .01, .02, .05, .1, .2%) Only 4 dilution tubes were included in each test run. |
| Test products | Buffered pH6 4% Stanhexidine (composition of Example 2) & 4% Hibitane (Ayerst) hand cleanser products |

| Exposure | |
|---|---|
| Neutralizer | Sterile 1% Lecithin (Sigma) + 1% Tween 80 (Sigma) aqueous solution |
| Diluent | Sterile distilled water |

| Scheme for preparing dilutions of disinfectant | | | | | |
|---|---|---|---|---|---|
| | Disinfectant | | | D.W. | Final |
| Step | Conc. | Source | Vol* | Vol* | Conc. |
| 1 | 4000 ug/ml | 4% stock | 4 ml | 36 ml | 4000 ug/ml |
| 2 | 4000 | step 1 | 10 | 10 | 2000 |
| 3 | 4000 | step 1 | 5 | 15 | 1000 |
| 4 | 4000 | step 1 | 4 | 36 | 400 |
| 5 | 400 | step 4 | 10 | 10 | 200 |
| 6 | 400 | step 4 | 5 | 15 | 100 |
| 7 | 200 | step 5 | 2 | 18 | 20 |
| 8 | 20 | step 7 | 2 | 18 | 2 |

*Volume prepared was changed proportionally according to number of strains tested.

The Test Procedure was as follows:

1) Double (2×) strength disinfectant dilutions were made according to the table presented above. Four appropriate dilutions in each test system were then chosen and 2 ml of each dilution was delivered into tubes A, B, C, D respectively, and 2 ml D.W. as control into tube E.

2) About 15 ml of bacterial suspension was made at the range of 1-3×10$^8$ CFU/ml (No. 1 to No. 3 of McFarland Standards).

3) Thirteen tubes of 9 ml 1% neutralizer solutions were prepared (12 tubes for test, 1 tube for control).

4) Two ml of bacterial suspension (from step 2) was added to each of the tubes A, B, C, D (from step 1) at 15 seconds intervals. Two ml was added to tube E as control.

5) All tubes were mixed vigorously by mixer.

6) At time one minute (T1), two minutes (T2) and five minutes (T5), 1 ml of the mixture of bacterial suspension and disinfectant dilution from tube A, B, C, & D was delivered at 15 second time intervals to corresponding tubes of 9 ml neutralizer (from step 3) in order to stop the disinfecting activities at fixed time exposure.

7) One ml of mixture in tube E was added into a fresh 9 ml neutralizer tube labelled as tube F.

8) All neutralizer tubes were mixed vigorously by mixer after steps 6 & 7.

9) A viable colony count was performed on each tube from step 6 by subculturing 20 ul from each tube onto a corresponding labelled pre-dried quadrant plate (T1 tubes→T1 plate, T2 tubes→T2 plate, T3 tubes→T3 plate) in duplicate or triplicate.

10) End point viable colony count standards were prepared using tube F (from step 7) as 100% count standard. One percent, 0.1%, 0.01%, 0.001% count standards were also prepared.

11) Viable colony counts were performed on all the standards (from step 10) by subculturing 20 ul from each viable count standard tube onto a pre-dried quadrant plate.

12) All plates were inverted and incubated after the 20 ul drops had been absorbed at 37° C. for overnight.

13) The MLC end point was read as the lowest disinfectant concentration at a particular time exposure showing smaller cell count than that in 20 ul drop areas in 0.01% quadrant of the standard quadrant plate.

The results obtained are as follows:

| Organism | | Time Min. | 4% Stanhexidine ug/ml | 4% Hibitane ug/ml |
|---|---|---|---|---|
| FUNGI: | | | | |
| #1 | Aspergillus fumigatus D5 | 1 | >2000 | >2000 |
| | | 2 | >2000 | >2000 |
| | | 5 | 2000 | >2000 |
| #2 | *Candida albicans 10231 | 1 | 200 | 200 |
| | | 2 | 200 | 200 |
| | | 5 | 100 | 200 |
| #3 | C. albicans D3 | 1 | 200 | 200 |
| | | 2 | 200 | 200 |
| | | 5 | 200 | 100 |
| GRAM POSITIVE BACTERIA: | | | | |
| #4 | Bacillus sp. B52 | 1 | >2000 | >2000 |
| | | 2 | >2000 | >2000 |
| | | 5 | >2000 | >2000 |
| #5 | Corynebacterium diphtheriae B43 (non-toxigenic) | 1 | 50 | 100 |
| | | 2 | 50 | 50 |
| | | 5 | 50 | 50 |
| #6 | Diphtheroid B44 | 1 | 50 | 50 |
| | | 2 | 50 | 50 |
| | | 5 | 50 | 50 |
| #7 | *Enterococcus sp. 29212 | 1 | 100 | 200 |
| | | 2 | 100 | 200 |
| | | 5 | 100 | 100 |
| #8 | Enterococcus sp. 1A3 | 1 | 50 | 200 |
| | | 2 | 50 | 200 |
| | | 5 | 10 | 200 |
| #9 | Enterococcus sp. 2D7 | 1 | 50 | 200 |
| | | 2 | 50 | 200 |
| | | 5 | 50 | 200 |
| #10 | Listeria monocytogenes 1D6 | 1 | 50 | 100 |
| | | 2 | 50 | 50 |
| | | 5 | 10 | 50 |
| #11 | L. monocytogenes 3D1 | 1 | 50 | 200 |
| | | 2 | 50 | 100 |
| | | 5 | 50 | 50 |
| #12 | *Staphylococcus aureus 6538 | 1 | 10 | 50 |
| | | 2 | 10 | 50 |
| | | 5 | 10 | 10 |
| #13 | *S. aureus 25923 | 1 | 100 | 200 |
| | | 2 | 100 | 100 |
| | | 5 | 100 | 100 |
| #14 | *S. aureus 29213 | 1 | 100 | 100 |
| | | 2 | 100 | 100 |
| | | 5 | 100 | 100 |
| #15 | S. aureus #1 QC ( MRSA) | 1 | 100 | 200 |
| | | 2 | 100 | 100 |
| | | 5 | 100 | 100 |
| #16 | S. aureus #5 ( MRSA) | 1 | 50 | 200 |
| | | 2 | 50 | 100 |
| | | 5 | 10 | 100 |
| #17 | S. aureus #9 ( MRSA) | 1 | 50 | 100 |
| | | 2 | 50 | 100 |
| | | 5 | 10 | 100 |
| #18 | *Staphylococcus epidermidis 29887 | 1 | 50 | 100 |
| | | 2 | 50 | 50 |
| | | 5 | 10 | 50 |
| #19 | Staphylococcus haemolyticus QC | 1 | 100 | 50 |
| | | 2 | 100 | 50 |
| | | 5 | 50 | 50 |
| #20 | Streptococcus pneumoniae B53 | 1 | 50 | 50 |
| | | 2 | 50 | 50 |
| | | 5 | 50 | 50 |
| #21 | Streptococcus pyogenes β-Haemolytic (Group A) | 1 | 50 | 100 |
| | | 2 | 50 | 100 |
| | | 5 | 50 | 50 |
| #22 | Streptococcus sp. B54 α-Haemolytic (viridans Group) | 1 | 50 | 50 |
| | | 2 | 50 | 50 |
| | | 5 | 50 | 50 |
| #23 | Streptococcus β-Haemolytic (Group G) | 1 | 50 | 50 |
| | | 2 | 50 | 50 |
| | | 5 | 50 | 50 |
| GRAM NEGATIVE BACTERIA: | | | | |
| #24 | Acinetobacter sp. C42 | 1 | 50 | 100 |
| | | 2 | 50 | 100 |
| | | 5 | 10 | 100 |
| #25 | Acinetobacter sp. 6C10 | 1 | 50 | 100 |
| | | 2 | 50 | 100 |
| | | 5 | 10 | 100 |
| #26 | Acinetobacter sp. 9E8 | 1 | 50 | 50 |
| | | 2 | 50 | 50 |
| | | 5 | 10 | 50 |
| #27 | Aeromonas hydrophila C125 | 1 | 50 | 50 |
| | | 2 | 50 | 50 |
| | | 5 | 50 | 50 |
| #28 | Campylobacter jejuni B47 | 1 | 50 | 50 |
| | | 2 | 50 | 50 |
| | | 5 | 50 | 50 |
| #29 | Citrobacter freundii C89 | 1 | 50 | 50 |
| | | 2 | 50 | 50 |
| | | 5 | 50 | 50 |
| #30 | *Enterobacter aerogenes 35029 | 1 | 50 | 100 |
| | | 2 | 50 | 100 |
| | | 5 | 50 | 100 |
| #31 | Enterobacter cloacae 1A5 | 1 | 200 | 100 |
| | | 2 | 100 | 100 |
| | | 5 | 50 | 100 |
| #32 | E. cloacae 9E5 | 1 | 50 | 100 |
| | | 2 | 50 | 100 |
| | | 5 | 50 | 100 |
| #33 | Enterobacter sp. 9E7 | 1 | 50 | 50 |
| | | 2 | 50 | 50 |
| | | 5 | 50 | 50 |
| #34 | *Escherichia coli 25922 | 1 | 50 | 100 |
| | | 2 | 50 | 50 |
| | | 5 | 50 | 50 |
| #35 | E. coli CO3 | 1 | 50 | 100 |
| | | 2 | 50 | 50 |
| | | 3 | 50 | 50 |
| #36 | E. coli C93 | 1 | 50 | 100 |
| | | 2 | 50 | 50 |
| | | 5 | 50 | 50 |
| #37 | E. coli C159 ( EPEC 0157:H7) | 1 | 50 | 100 |
| | | 2 | 50 | 100 |
| | | 5 | 50 | 100 |
| #38 | Haemophilus influenzae B49 | 1 | 50 | 50 |
| | | 2 | 50 | 50 |
| | | 5 | 50 | 50 |
| #39 | H. influenzae B51 (β Lactamase +) | 1 | 100 | 100 |
| | | 2 | 100 | 100 |
| | | 5 | 100 | 100 |
| #40 | Haemophilus parainfluenzae B57 | 1 | 50 | 50 |
| | | 2 | 50 | 50 |
| | | 5 | 50 | 50 |
| #41 | Hafnia alvei C50 | 1 | 50 | 200 |
| | | 2 | 50 | 100 |
| | | 5 | 50 | 100 |
| #42 | Klebsiella oxytoca C88 | 1 | 50 | 200 |
| | | 2 | 50 | 100 |
| | | 5 | 10 | 100 |
| #43 | *Klebsiella pneumoniae 33495 | 1 | 50 | 100 |
| | | 2 | 50 | 100 |
| | | 5 | 50 | 100 |
| #44 | Klebsiella sp. 8E8 | 1 | 50 | 100 |
| | | 2 | 50 | 100 |
| | | 5 | 50 | 100 |
| #45 | Morganella morganii C69 | 1 | 50 | 100 |
| | | 2 | 200 | 100 |
| | | 5 | 200 | 100 |
| #46 | Neisseria gonorrhoeae B55 | 1 | 10 | 10 |
| | | 2 | 10 | 10 |
| | | 5 | 10 | 10 |
| #47 | Neisseria meningtidis B56 | 1 | 50 | 50 |
| | | 2 | 50 | 50 |
| | | 5 | 50 | 50 |
| #48 | Pasteurella multocida C57 | 1 | 50 | 50 |
| | | 2 | 50 | 50 |
| | | 5 | 50 | 50 |
| #49 | Proteus mirabilis C148 | 1 | 100 | 100 |
| | | 2 | 100 | 100 |
| | | 5 | 100 | 100 |
| #50 | P. mirabilis C150 | 1 | 100 | 100 |
| | | 2 | 100 | 100 |
| | | 5 | 100 | 100 |
| #51 | Proteus vulgaris C150 | 1 | 100 | 100 |
| | | 2 | 100 | 100 |
| | | 5 | 100 | 100 |
| #52 | Providencia | 1 | 100 | 200 |

-continued

| Organism | | Time Min. | 4% Stanhexidine ug/ml | 4% Hibitane ug/ml |
|---|---|---|---|---|
| | alcalifaciens P-O:61 | 2 | 100 | 200 |
| | | 5 | 100 | 200 |
| #53 | Providencia | 1 | 100 | 200 |
| | rettigeri ST.J.54 | 2 | 100 | 200 |
| | | 5 | 100 | 200 |
| #54 | Providencia | 1 | 100 | 200 |
| | stuartii M29 | 2 | 100 | 100 |
| | | 5 | 100 | 100 |
| #55 | P. stuartii M170 | 1 | 200 | 100 |
| | | 2 | 100 | 100 |
| | | 5 | 100 | 100 |
| #56 | P. stuartii 2D6 | 1 | 200 | >2000 |
| | | 2 | 100 | >2000 |
| | | 5 | 100 | 2000 |
| #57 | *Pseudomonas | 1 | 100 | 100 |
| | aeruginosa 15442 | 2 | 100 | 100 |
| | | 5 | 100 | 100 |
| #58 | *P. aeruginosa 27853 | 1 | 200 | 100 |
| | | 2 | 200 | 100 |
| | | 5 | 100 | 100 |
| #59 | P. aeruginosa 1A1 | 1 | 50 | 50 |
| | | 2 | 50 | 50 |
| | | 5 | 50 | 50 |
| #60 | P. aeruginosa 2D5 | 1 | 100 | 100 |
| | | 2 | 100 | 100 |
| | | 5 | 100 | 100 |
| #61 | P. aeruginosa 3E5 | 1 | 100 | 100 |
| | | 2 | 100 | 100 |
| | | 5 | 100 | 100 |
| #62 | Salmonella sp. C139 (Group D) | 1 | 50 | 100 |
| | | 2 | 50 | 100 |
| | | 5 | 50 | 100 |
| #63 | *Salmonella typhi 6539 | 1 | 50 | 50 |
| | | 2 | 50 | 50 |
| | | 5 | 50 | 50 |
| #64 | Serratia marcescens C66 | 1 | 200 | 50 |
| | | 2 | 50 | 50 |
| | | 3 | 50 | 50 |
| #65 | S. marcescens 3A3 | 1 | 50 | 100 |
| | | 2 | 50 | 50 |
| | | 5 | 50 | 50 |
| #66 | Shigella sonnei C157 | 1 | 50 | 100 |
| | | 2 | 50 | 100 |
| | | 5 | 50 | 100 |
| #67 | Vibrio parahaemolyticus 8C6 | 1 | 50 | 50 |
| | | 2 | 50 | 50 |
| | | 5 | 50 | 50 |
| #68 | Xanthomonas maltophilia 3A6 | 1 | 100 | 200 |
| | | 2 | 100 | 100 |
| | | 5 | 100 | 50 |
| #69 | X. maltophilia 3E6 | 1 | 50 | 50 |
| | | 2 | 50 | 50 |
| | | 5 | 50 | 50 |
| #70 | Yersinia enterocolitica C158 | 1 | 50 | 100 |
| | | 2 | 50 | 100 |
| | | 5 | 50 | 100 |

* = ATCC QC strains
= Methicillin resistant *Staphylococcus aureus*
= Multiple antibiotic resistant VGH isolates
= Enteropathogenic *Escherichia coli* causes hemorrhagic colitis disease The rest of the test strains are the routine hospital isolates.

It is apparent from these results that in approximately 39% of the 70 aerobic organisms tested, that is, 27 organisms, the antiseptic composition of the present invention was superior in terms of the killing or cidal activity as compared to the Hibitane composition. In approximately 56% of the 70 organisms tested, that is, 39 organisms the antiseptic composition of the present invention was equivalent in its cidal activity as compared to the Hibitane composition. Accordingly, in approximately 95% of the organisms tested, the antiseptic composition of the present invention showed equivalent or superior cidal activity. It is noteworthy that the Hibitane composition exhibited better cidal activity on only four organisms out of the 70 tested (6%).

EXAMPLE IV

Analysis of Cidal Activity of Antiseptic Composition

Following the procedure outlined in Example III, a further Time Kill Analysis of the cidal activity of the composition was assessed. The results are as follows:

| | MLC RESULTS | | | |
|---|---|---|---|---|
| Organism | | Time Min. | 4% Stanhexidine | 4% Hibitane |
| FUNGI: | | | | |
| #1 | Candida albican B8280 | 1 | >2000 | >2000 |
| | | 2 | >2000 | >2000 |
| | | 5 | 500 | 200 |
| #2 | *Cryptococcus neoformans 32045 | 1 | 100 | 200 |
| | | 2 | 100 | 200 |
| | | 5 | 100 | 200 |
| #3 | *Saccharomyces cerevisiae 9763 | 1 | 100 | 100 |
| | | 2 | 100 | 100 |
| | | 5 | 100 | 100 |
| #4 | *Schizosaccharomyces pombe 2476 | 1 | >2000 | 500 |
| | | 2 | >2000 | 200 |
| | | 5 | 500 | 200 |
| GRAM POSITIVE BACTERIA: | | | | |
| #5 | *Bacillus cereus 11778 | 1 | >2000 | >2000 |
| | | 2 | >2000 | >2000 |
| | | 5 | >2000 | >2000 |
| #6 | *Bacillus subtilis 6633 | 1 | >2000 | >2000 |
| | | 2 | >2000 | >2000 |
| | | 5 | >2000 | >2000 |
| #7 | Corynebacterium group JK 3C3 | 1 | 200 | 200 |
| | | 2 | 100 | 100 |
| | | 5 | 50 | 100 |
| #8 | Staphylococcus epidermidis 10E4 | 1 | 50 | 100 |
| | | 2 | 50 | 100 |
| | | 5 | 50 | 100 |
| #9 | Streptococcus pneumoniae 8D6 | 1 | 50 | 100 |
| | | 2 | 50 | 100 |
| | | 5 | 50 | 100 |
| GRAM NEGATIVE BACTERIA: | | | | |
| #10 | Aeromonas hydrophilia | 1 | 50 | 50 |
| | | 2 | 50 | 50 |
| | | 5 | 50 | 50 |
| #11 | Alcaligenes ordorans W11269 | 1 | >2000 | 1000 |
| | | 2 | >2000 | 500 |
| | | 5 | >2000 | 200 |
| #12 | Flavobacterium odoratum 9A1 | 1 | 100 | 200 |
| | | 2 | 100 | 200 |
| | | 5 | 100 | 200 |
| #13 | Haemophilus influenzae B60 | 1 | 100 | 100 |
| | | 2 | 100 | 100 |
| | | 5 | 100 | 100 |
| #14 | Pseudomonas capacia 31BE9 | 1 | >2000 | >2000 |
| | | 2 | >2000 | >2000 |
| | | 5 | >2000 | >2000 |
| #15 | P. cepacia 30BE6 | 1 | >2000 | 500 |
| | | 2 | >2000 | 200 |
| | | 5 | >2000 | 200 |
| #16 | P. cepacia 29BA1 | 1 | >2000 | 1000 |
| | | 2 | >2000 | 500 |
| | | 5 | >2000 | 500 |
| #17 | Serratia marcescans (pigmented) C161 | 1 | 100 | 200 |
| | | 2 | 100 | 100 |
| | | 5 | 100 | 100 |
| #18 | Vibrio vulnificus 8C9 | 1 | 10 | 50 |
| | | 2 | 10 | 50 |
| | | 5 | 10 | 50 |
| ANAEROBIC BACTERIA: | | | | |
| #19 | *Bacteriodes fragilis 25285 | 1 | 50 | 100 |
| | | 2 | 50 | 100 |
| | | 5 | 50 | 100 |
| #20 | B. fragilis group W9613 | 1 | 50 | 100 |
| | | 2 | 50 | 100 |
| | | 5 | 50 | 100 |
| #21 | B. fragilis group W9240 | 1 | 50 | 100 |
| | | 2 | 50 | 100 |
| | | 5 | 50 | 100 |

-continued

MLC RESULTS

| Organism | | Time Min. | 4% Stanhexidine | 4% Hibitane |
|---|---|---|---|---|
| #22 | *Bacteriodes thetaiotaomicron 29741 (0319) | 1 | 50 | 100 |
| | | 2 | 50 | 100 |
| | | 5 | 50 | 100 |
| #23 | *Clostridium botulinum (Non-toxigenic) 25766 | 1 | >2000 | 2000 |
| | | 2 | >2000 | 2000 |
| | | 5 | >2000 | 2000 |
| #24 | *Clostridium difficile 9689 | 1 | 50 | 50 |
| | | 2 | 50 | 50 |
| | | 5 | 50 | 50 |
| #25 | C. difficile 2CD C3 | 1 | 200 | 200 |
| | | 2 | 200 | 200 |
| | | 5 | 200 | 200 |
| #26 | *Clostridium perfringens 13124 | 1 | 50 | 200 |
| | | 2 | 50 | 200 |
| | | 5 | 50 | 100 |
| #27 | C. perfringens W8942 | 1 | >2000 | >2000 |
| | | 2 | >2000 | >2000 |
| | | 5 | >2000 | >2000 |
| #28 | *Clostridium tetani 19406 | 1 | 50 | 50 |
| | | 2 | 50 | 50 |
| | | 5 | 50 | 10 |
| #29 | Aspergillus niger ATCC 16404 | 1 | 2000 | 2000 |
| | | 2 | 2000 | 2000 |
| | | 5 | 2000 | 2000 |
| #30 | Legionella pneumophila ATCC 33153 serogroup 1 | 1 | 200 | 500 |
| | | 2 | 100 | 200 |
| | | 5 | 100 | 100 |
| #31 | Legionella pneumophila R1069 serogroup 1 | 1 | 50 | 200 |
| | | 2 | 50 | 200 |
| | | 5 | 10 | 100 |
| #32 | Neisseria gonorrhoeae CDC 98 | 1 | 50 | 50 |
| | | 2 | 50 | 50 |
| | | 5 | 50 | 50 |
| #33 | Neisseria meningitidis B59 | 1 | 50 | 50 |
| | | 2 | 50 | 50 |
| | | 5 | 50 | 50 |
| #34 | Alcaligenes faecalis ATCC 8750 | 1 | >2000 | 200 |
| | | 2 | 2000 | 200 |
| | | 5 | 500 | 200 |
| #35 | Alcaligenes denitrificans C166 | 1 | >2000 | 500 |
| | | 2 | >2000 | 500 |
| | | 5 | >2000 | 200 |
| #36 | Flavobacterium meningosepticum C163 | 1 | 100 | 100 |
| | | 2 | 100 | 50 |
| | | 5 | 100 | 50 |
| #37 | Flavobacterium sp. Group IIh C165 | 1 | 50 | 100 |
| | | 2 | 50 | 100 |
| | | 5 | 50 | 100 |
| #38 | Microsporum canis 36299 | 1 | 50 | 50 |
| | | 2 | 50 | 50 |
| | | 5 | 50 | 50 |
| #39 | Microsporum gypseum 14683 | 1 | 50 | 50 |
| | | 2 | 50 | 50 |
| | | 5 | 50 | 50 |
| #40 | Penicillium notatum 9478 | 1 | 100 | 100 |
| | | 2 | 100 | 100 |
| | | 5 | 100 | 100 |
| #41 | Enterococcus faecalis 29212 | 1 | 100 | 200 |
| | | 2 | 100 | 200 |
| | | 5 | 100 | 100 |
| #42 | Proteus vulgaris C162 | 1 | 100 | 100 |
| | | 2 | 100 | 100 |
| | | 5 | 100 | 100 |

*ATCC QC Strains

It is apparent from these results that in approximately 33% of the organisms tested, including anaerobes, the antiseptic composition of the present invention (Stanhexidine) was superior in terms of killing or cidal activity as compared to Hibitane. In approximately 67% of the 42 organisms tested, that is, 28 organisms, the antiseptic composition of the present invention showed equal or superior cidal activity as compared to Hibitane. Hibitane exhibited superior activity on only 6 of the 42 organisms (14%).

We claim:

1. An antiseptic composition comprising a chlorhexidine cidal agent and a surfactant consisting of the alkyl phenyl macrogol ether nonoxinol 9, wherein the antiseptic composition comprises 5%–30% by weight nonoxinol 9 and 0.5%–10% by weight chlorhexidine, wherein a significant quantity of other nonionic or cationic surfactants are not present.

2. The composition according to claim 1 wherein chlorhexidine is selected from the group comprising a water-soluble gluconate, acetate, hydrochloride, glutamate, succinate, iminodiacetate, and acetamidohexanoate.

3. A method of killing or inhibiting the growth of bacteria at an application site, which comprises adding to the application site an antibacterial effective amount of a composition comprising a chlorhexidine cidal agent and a surfactant consisting of the alkyl phenyl macrogol ether nonoxinol 9, wherein the antiseptic composition comprises 5%–30% by weight nonoxinol 9 and 0.5%–10% by weight chlorhexidine, wherein a significant quantity of other nonionic or cationic surfactants are not present, and wherein the bacteria are selected from among Staphylococcus aureus and methicillin-resistant strains thereof.

4. The composition according to claim 3 comprising 2% by weight chlorhexidine and 7.5% by weight nonoxinol 9.

5. The composition according to claim 3 comprising 4% by weight chlorhexidine and 15% by weight nonoxinol 9.

6. The composition according to claim 1 additionally comprising at least one emollient.

7. The composition according to claim 6 wherein the emollient is selected from the group comprising glycerin and polyhydric compounds selected from the group comprising sorbitol, mannitol and carboxy vinyl polymers.

8. The composition according to claim 1 additionally comprising at least one thickener.

9. The composition according to claim 8 wherein the thickener is selected from the group comprising fatty acid alkyloamides selected from the group comprising coconut oil mono- or diethanolamide, coconut oil mono- or di- isopropanolamide, coconut oil diglycolamide, oleic diethanolamide and lauric diethanolamide and fatty amine oxides selected from the group comprising dimethyl cocamide oxide, dimethyl lauryl amine oxide, and dimethyl oleyl amine oxide.

10. The composition according to claim 1 additionally comprising at least one colouring agent.

11. The composition according to claim 10 wherein the colouring agent is selected from the group comprising amaranth and sunset yellow.

12. The composition according to claim 1 having a pH of about 6.

13. The composition according to claim 1 additionally comprising at least one moisture-retaining agent.

14. The composition according to claim 13 wherein the agent is selected from fatty alcohols such as cetyl alcohol and stearyl alcohol.

15. The composition of claim 1 including at least one buffering agent.

16. The composition according to claim 15 wherein the buffering agents are citric acid and sodium citrate.

17. The composition according to claim 1 including at least one other cidal agent.

18. A process for preparing an antiseptic composition which comprises: mixing in aqueous solution a chlorhexidine cidal agent and a surfactant consisting of the alkyl phenyl macrogol ether nonoxinol 9, to prepare an antiseptic composition comprising 5%–30% by weight nonoxinol 9 and 0.5%–10% by weight chlorhexidine, wherein a significant quantity of other nonionic or cationic surfactants are not present.

19. The process according to claim 18 wherein chlorhexidine is selected from the group comprising a water-soluble gluconate, acetate, hydrochloride, glutamate, succinate, iminodiacetate, and acetamido hexanoate.

20. A process in which the antiseptic composition of claim 18 issued as a hand cleaner.

* * * * *

UNITED STATES PATENT AND TRADEMARK OFFICE
CERTIFICATE OF CORRECTION

PATENT NO. : 5,308,611
DATED : May 3, 1994
INVENTOR(S) : C. B. H. Thompson

Page 1 of 2

It is certified that error appears in the above-indentified patent and that said Letters Patent is hereby corrected as shown below:

| COLUMN | LINE | |
|---|---|---|
| 1 | 68 | "(MLC" should read --(MLC)-- |
| 8 | 33 | "(  EPEC 0157:H7)" should read --(■ EPEC 0157:H7)-- |
| 8 | 49 | "#44   Klebsiella sp. 8E8" should read --#44 ♦ Klebsiella sp. 8E8-- |
| 8 | 51 | "#45 Morganella   1   50   100" should read --#45 Morganella  1   200   100-- |
| 9 | 14 | "#56   P. stuartii 2D6" should read --#56 ♦ P. stuartii 2D6-- |
| 9 | 21 | "#59   P. aeruginosa 1A1" should read --#59 ♦ P. aeruginosa 1A1-- |
| 9 | 24 | "#60   P. aeruginosa 2D5" should read --#60 ♦ P. aeruginosa 2D5-- |
| 9 | 26 | "#61   P. aeruginosa 3E5" should read --#61 ♦ P. aeruginosa 3E5-- |
| 9 | 52 | "  = Methicillin resistant *Staphylococcus aureus*" should read --● = Methicillin resistant *Staphylococcus aureus*-- |

UNITED STATES PATENT AND TRADEMARK OFFICE
CERTIFICATE OF CORRECTION

PATENT NO. : 5,308,611
DATED : May 3, 1994
INVENTOR(S) : C. B. H. Thompson

Page 2 of 2

It is certified that error appears in the above-indentified patent and that said Letters Patent is hereby corrected as shown below:

| COLUMN | LINE | |
|---|---|---|
| 9 | 53 | " = Multiple antibiotic resistant VGH isolates" should read<br>--♦ = Multiple antibiotic resistant VGH isolates-- |
| 9 | 54 | " = Enteropathogenic *Escherichia coli* causes hemorrhagic colitis disease" should read<br>--■ = Enteropathogenic *Escherichia coli* causes hemorrhagic colitis disease-- |
| 14<br>(Claim 19 Line 4) | 6 | "acetamido hexanoate" should read<br>--acetamidohexanoate-- |
| 14<br>(Claim 20 Line 2) | 8 | "claim 18" should read --claim 1-- |
| 14<br>(Claim 20 Line 2) | 8 | after "claim 1" insert --is used-- |

Signed and Sealed this

Sixth Day of September, 1994

Attest:

BRUCE LEHMAN

*Attesting Officer*     *Commissioner of Patents and Trademarks*